United States Patent [19]

Kamegai et al.

[11] Patent Number: 5,753,600
[45] Date of Patent: May 19, 1998

[54] LIQUID DETERGENT COMPOSITION

[75] Inventors: Jun Kamegai, Ichikawa; Hisataka Kobayashi, Utsunomiya; Toshie Takahashi, Tokyo; Takashi Imamura, Funabashi; Sachio Naito, Ichikai-machi, all of Japan

[73] Assignee: Kao Corporation, Tokyo, Japan

[21] Appl. No.: 340,451

[22] Filed: Nov. 14, 1994

Related U.S. Application Data

[63] Continuation of Ser. No. 48,502, Apr. 20, 1993, abandoned, which is a continuation of Ser. No. 769,498, Oct. 1, 1991, Pat. No. 5,234,618, which is a continuation of Ser. No. 588,859, Sep. 27, 1990, abandoned.

[51] Int. Cl.$^6$ .............................. C11D 1/722; C11D 3/22; C11D 3/26; C11D 3/48
[52] U.S. Cl. .......................... 510/131; 510/119; 510/127; 510/128; 510/129
[58] Field of Search ..................... 252/174.17, 550, 252/106, DIG. 13; 510/119, 127, 128, 129, 131

[56] References Cited

U.S. PATENT DOCUMENTS

| | | | |
|---|---|---|---|
| 4,048,181 | 9/1977 | Douglass | 260/294.8 |
| 4,536,188 | 8/1985 | Cook et al. | 252/174.17 |
| 4,599,188 | 7/1986 | Llenado | 252/174.17 |
| 4,632,991 | 12/1986 | Maurer et al. | 546/6 |
| 4,711,775 | 12/1987 | Dittmar et al. | 424/70 |
| 4,854,335 | 8/1989 | Inman | 132/209 |
| 4,885,107 | 12/1989 | Wetzel | 252/106 |
| 4,927,563 | 5/1990 | McCall | 252/551 |
| 5,015,414 | 5/1991 | Kamegai et al. | 252/545 |
| 5,057,311 | 10/1991 | Kamegai et al. | 424/70 |
| 5,062,989 | 11/1991 | Kamegai et al. | 252/174.17 |
| 5,151,209 | 9/1992 | McCall | 252/174.15 |
| 5,154,850 | 10/1992 | Deguchi et al. | 252/174.17 |

FOREIGN PATENT DOCUMENTS 0761171  11/1956  United Kingdom .

*Primary Examiner*—Glenn Caldarola
*Assistant Examiner*—Alexander G. Ghyka
*Attorney, Agent, or Firm*—Oblon, Spivak, McClelland, Maier & Neustadt, P.C.

[57] ABSTRACT

A detergent composition comprising (a) 0.1 to 95% by weight of a saccharide nonionic surfactant and (b) 0.01 to 5% by weight of an antibacterial agent. The detergent compositions are outstandingly mild to the skin, exhibiting a high antibacterial effect, without influencing or weakening the cutaneous metabolic and barrier functions of the skin. The detergent compositions can effectively restrain the early occurrence of dandruff after shampooing when used as detergents for the scalp and the hair. They also exhibit high antibacterial effect when used as body detergents.

6 Claims, No Drawings

LIQUID DETERGENT COMPOSITION

This application is a Continuation of application Ser. No. 08/048,502, filed on Apr. 20, 1993, now abandoned, which is a Continuation of application Ser. No. 07/769,498, filed on Oct. 1, 1991, now U.S. Pat. No. 5,234,618, which is a continuation of application Ser. No. 07/588,859, filed on Sep. 27,1990, now abandoned.

BACKGROUND OF THE INVENTION

1. Field of the Invention

This invention relates to a liquid detergent composition, and, more particularly, to a liquid detergent composition having low irritation to the skin, exhibiting an excellent antibacterial effect, and particularly giving superior anti-dandruff and deodorant effects when used as a detergent for washing the scalp and hair.

2. Description of the Background Art

Conventionally, synthetic anionic surfactants such as alkyl sulfates, ethoxylated alkyl sulfates have widely been used in liquid detergent compositions for skin and hair. They are excellent in detergency and foaming capability, however, they have a drawback of strong irritation to the skin and hair. The irritation of these surfactants closely relates to a skin-barrier function and to cell division of keratinocytes. There has been a report [Gibson W. T. et al., Food Chem. Toxic., 23, 103, (1985)] that a skin-barrier function is lowered and cell division of keratinocytes is promoted with increased irritation of surfactants.

In the meantime, it is believed that dandruff is mostly caused by abnormal desquamation of horny cells and sebaceous hypersecretion and worsened by the growth of bacteria. For anti-dandruff shampoo compositions, therefore, synthetic anionic-surfactants and an antibacterial agent are usually incorporated to wash the secretive sebum and restrain the growth of bacteria. However, dandruff is often developed in a relatively short time after shampooing, although they frequently shampoo the hair and scalp with these anti-dandruff shampoo compositions. This is because the more frequent shampooing increases the chances of contacting surfactants having high irritation to the skin with the scalp, thus irritating the skin and lowering a barrier function of the skin, and promoting cell division of keratinocytes resulting in the acceleration of the development of dandruff.

As for body detergent compositions, most of these detergent compositions usually contain highly irritant surfactants. These surfactants inevitably give an adverse effect on a skin-barrier function. In this respect, washing the skin with these detergents consequently weaken the resistance of the skin against external stimuli such as microbial contagion to the skin.

From the above facts, the development of detergent compositions which can restrain dandruff and never weaken the resistance of the skin against external stimuli has been desired.

In view of this situation, the present inventors have undertaken extensive studies to resolve the above-mentioned problem. As a result, the inventors have found that by incorporating a saccharide nonionic surfactant and an antibacterial agent into a detergent composition, the above-mentioned problem could be solved and also an antibacterial effect of the detergent composition was greatly improved. This finding has led to the completion of this invention.

SUMMARY OF THE INVENTION

Accordingly, an object of this invention is to provide a detergent composition comprising:

(a) 0.1 to 95% by weight of a saccharide nonionic surfactant, and (b) 0.01 to 5% by weight of an antibacterial agent.

Other objects, features and advantages of the invention will hereinafter become more readily apparent from the following description.

DETAILED DESCRIPTION OF THE INVENTION AND PREFERRED EMBODIMENTS

Given as examples of saccharide nonionic surfactants which are an essential component of the present invention are the following compounds (A-1) and (A-2):

(A-1) alkyl saccharide surfactants represented by formula (I),

$$R_1-O-(R_2O)_m-G_n \qquad (I)$$

wherein $R_1$ represents a linear or branched alkyl, alkenyl, or alkylphenyl group having 6–18 carbon atoms, $R_2$ represents an alkylene group having 2–4 carbon atoms, G is a reducing sugar having 5–6 carbon atoms, m denotes a value of 0–10, and n denotes a value of 1–10.

For $R_1$ in formula (I), among linear or branched alkyl, alkenyl, or alkylphenyl groups having 6–18 carbon atoms, linear or branched alkyl groups having 9–14 carbon atoms such as decyl-, lauryl-, myristyl group are particularly preferable from the aspect of detergent performances such as foaming capability and the like. The value of m in formula (I), which is a polymerization degree of alkylene oxide, can be 0 to 10, but is preferably from 0 to 3 and particularly preferably 0 from the aspect of detergent performances such as foaming capability and the like. The basic unit of the saccharide portion, i.e., G in formula (I), which is the hydrophilic group of the alkyl saccharide surfactant, is a reducing sugar having 5–6 carbon atoms. Glucose, galactose, and fructose are named as examples of desirable reducing sugars. The degree of polymerization of saccharide (S), i.e., the value of n in formula (I), is 1 to 10. In particular, the use of alkyl saccharide surfactants containing 80% or more of saccharide portion having the degree of polymerization (S) of 1 to 4 is desirable. When the influence of both the polymerization (S) and the group $R_1$ on the compound (I) are taken into account, the desirable value of (S) is 1 to 1.4 when the $R_1$ group is $C_{8-11}$, and 1.5 to 4.0 when the $R_1$ group is $C_{12-14}$. The mean value of (S) is determined by the proton-NMR method. Given as specific examples of alkyl saccharide surfactants are those synthesized by the Koenings-Knorr method such as β-glucoside, e.g., octylglucoside, nonylglucoside, decylmaltoside, dodecylmaltoside, polyoxyethylene(3 E.O.)dodecylglucoside, and the like. Included also as these alkyl saccharide surfactants are those synthesized from a reducing sugar such as glucose, galactose, maltose, fructose, or the like and a natural alcohol, higher alcohol synthesized by oxo synthesis, and higher alcohol of polyoxyethylene oxide adduct (U.S. Pat. No. 3,219,656, 3,839,318, and 4,223,129). Included further as these alkyl saccharide surfactants are alkyl fructoside and the like synthesized from sucrose and a higher alcohol by heat-alcoholysis reaction.

(A-2) saccharide amide surfactants represented by formula (II)

$$R_3-\underset{\underset{O}{\|}}{C}-\underset{\underset{R_4}{|}}{N}-X \qquad (II)$$

wherein $R_3$ represents a linear or branched alkyl, alkenyl, or alkylphenyl group having 5–17 carbon atoms, $R_4$ represents a hydrogen atom, a linear or branched alkyl or alkenyl group having 1–18 carbon atoms, a group

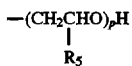

wherein $R_5$ represents a hydrogen atom or methyl group and p denotes a value of 0–10, or a group —$CH_2$—$CH_2$—OH,

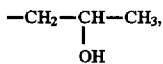

or —$CH_2$—$CH_2$—$CH_2$—OH, and X represents a polyhydroxyalkyl group derived from saccharide residue having 4–30 carbon atoms.

Among $R_3$ in formula (II), which represents a linear or branched alkyl., alkenyl, or alkylphenyl group having 5–17 carbon atoms, preferable examples are those of which a group

is induced from capric acid, caprylic acid, lauric acid, myristic acid, palmitic acid, stearic acid, isostearic acid and oleic acid, and particularly preferable are those from capric acid and lauric acid. Enumerated as examples of $R_4$ in formula (II) are a hydrogen atom, methyl group, ethyl group, n-propyl group, isopropyl group, n-butyl group, t-butyl group, n-hexyl group, octyl group, 2-ethylhexyl group, decyl group, dodecyl group, stearyl group, isostearyl group, polyethylene or polypropylene glycol with polymerization degree of 2–10, or 2-hydroxyethyl group, 2-hydroxypropyl group, 3-hydroxypropyl group, and the like. Among them, a hydrogen atom, methyl group, ethyl group, 2-hydroxyethyl group, 2-hydroxypropyl group, and 3-hydroxypropyl group are preferable. X in formula (II), which represents a polyhydroxyalkyl group having 4–30 carbon atoms, or may be a polyhydroxyalkyl group having 4–7 carbon atoms which is glucoside-bonded with a mono, di-, or oligo-saccharide. Given as examples of these polyhydroxyalkyl groups are 1-deoxyerythrityl group, 1-deoxyarabityl group, 1-deoxyxyltyl group, 1-deoxysorbityl group, 2-deoxysorbitol-2-yl group, 1-deoxymannityl group, 2-deoxymannitol-2-yl group, 1-deoxygalactyl group, 1-deoxy-4-galactoside-sorbityl group, 2-deoxy-4-glucoside-sorbitol-2-yl group, 2-deoxy-4-glucoside-mannitol-2-yl group, 1-deoxy-4-maltoglucoside-sorbityl group, 1-deoxy-4-oligoglucoside-sorbityl group, 1-deoxy-4-polyglucoside-sorbityl group, and the like. Among them, 1-deoxysorbityl group and 1-deoxy-4-glucoside-sorbityl group are preferable.

A saccharide nonionic surfactant can be incorporated in the detergent composition of the present invention in an amount of 0.1–95% by weight and preferably 5–20% by weight. If the amount is less than 0.1% by weight, the detergency will be insufficient while the amount exceeds 95% by weight, the detergency will not be improved any more.

Examples of antibacterial agents to be used in the present invention are the following compounds (B-1) –(B-7):

(B-1) calcium-, magnesium-, barium-, strontium-, zinc-, cadmium-, tin-, or zirconium salts of 2-mercapto-pyridine-N-oxide.

(B-2) 1-hydroxy-2-pyrrolidone derivatives represented by formula (III),

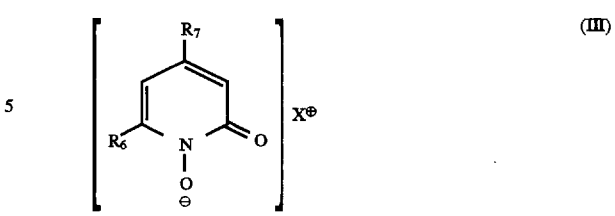

wherein $R_6$ represents an alkyl group having 1–17 carbon atoms, alkenyl group having 2–17 carbon atoms, cycloalkyl group having 5–8 carbon atoms, bicycloalkyl group having 7–9 carbon atoms, cycloalkyl-alkyl group wherein the alkyl group has 1–4 carbon atoms and the cycloalkyl group may be substituted with an alkyl group having 1–4 carbon atoms, aryl group, aralkyl group with an alkyl group having 1–4 carbon atoms, aryl-alkenyl group with the alkenyl group having 2–4 carbon atoms, aryloxyalkyl or arylmercaptoalkyl group with the alkyl group having 1–4 carbon atoms, benzhydryl group, phenylsulfonylalkyl group with the alkyl group having 1–4 carbon atoms, furylalkenyl group with the furyl or alkenyl group having 2–4 carbon atoms, wherein the above-mentioned aryl residual group may be substituted with an alkyl group having 1–4 carbon atoms, alkoxy group having 1–4 carbon atoms, nitro group, cyano group, or a halogen atom; $R_7$ represents a hydrogen atom, alkyl group having 1–4 carbon atoms, alkenyl group having 2–4 carbon atoms, halogen atom, phenyl group, or benzyl group; and $X^+$ represents an organic base, alkali metal ion, ammonium ion, alkaline earth metal ion, or a divalent to tetravalent cationic ion.

Given as examples of the compounds represented by formula (III) are those disclosed in Japanese Patent Laid-open No. 50142/1974: for example, 6-alkyl compounds such as 1-hydroxy-2-pyridone, 1-hydroxy-4-methyl-2- pyridone, 1-hydroxy-6-methyl-2-pyridone, 1-hydroxy-4,6-dimethyl-2-pyridone, 1-hydroxy-4-methyl-6-(2,4,4-trimethylpentyl)-2-pyridone; 6-cyclohexane compounds such as 1-hydroxy-4-methyl-6-cyclohexyl-2-pyridone, 1-hydroxy-4-methyl-6-(methyl-cyclohexyl)-2-pyridone, 1-hydroxy-4-methyl-6-(2-bicyclo[2,2,1]heptyl)-2-pyridone; 6-phenyl compounds such as 1-hydroxy-4-methyl-6-(4-methyl-phenyl)-2-pyridone,1-hydroxy-4-methyl-6-[1-(4-nitrophenoxy)-butyl]-2-pyridone, 1-hydroxy-4-methyl-6-(4-cyanophenoxymethyl)-2-pyridone, 1-hydroxy-4-methyl-6-(phenylsulfonylmethyl)-2-pyridone, 1-hydroxy-4-methyl-6-(4-bromo-benzyl)-2-pyridone, and the like. Among them, 6-alkyl compounds are preferable.

Compounds (III) may also be used as a salt of various organic or inorganic bases. Examples of these organic bases are low molecular alkanol amines, e.g. ethanolamine, diethanolamine, N-ethylethanolamine, triethanolamine, diethylaminoethanol, 2-amino-2-methyl-propanediol; non-volatile bases, e.g. ethylenediamine, hexamethylenediamine, cyclohexylamine, benzylamine, N-methylpiperazine; quaternary ammonium hydroxides, e.g. trimethylbenzyl hydroxide; guanidine and its derivatives, and especially their alkylated products; and the like. Given as examples of inorganic bases are salts of an alkali metal, e.g. sodium, potassium; ammonium salts, salts of an alkaline earth metal, e.g. magnesium, calcium; salts of a divalent to tetravalent cationic ion, e.g. zinc, aluminum, zirconium; and the like. Among the above-mentioned salts, non-volatile organic salts, e.g. low molecular alkanolamine, ethylenediamine; and inorganic salts, e.g. salts of an alkali metal are preferable.

(B-3) 2,2'-dithio-bis-(pyridine-N-oxide) represented by formula (IV),

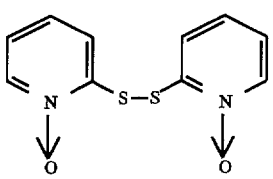
(IV)

The compounds represented by formula (IV) may incorporated as a complex salt with an inorganic salt in the detergent composition of the present invention. Examples of such inorganic salts are magnesium sulfate and the like.

(B-4) trichloro carbanide (TCC) represented by formula (V),

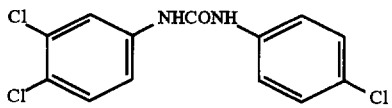
(V)

(B-5) trichlosan represented by formula (VI),

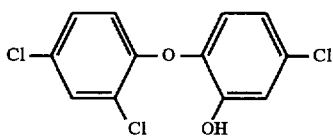
(VI)

(B-6) linear mono- or di-alkyl quaternary ammonium salts represented by formula (VII),

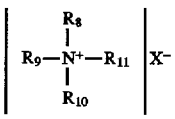
(VII)

wherein $R_8$–$R_{11}$ represent hydrocarbon groups, and one or two of $R_8$–$R_{11}$ have 8–24 carbon atoms and others are an alkyl or hydroxyalkyl group having 1–3 carbon atoms; and X⁻ represents a halogen atom, amino acid, fatty acid, an anionic residue of phosphate, phosphonate, sulfonate, or sulfate having an alkyl or alkenyl group of branched or straight 1–30 carbon atoms, and an anionic oligomer or polymer selected from formalin condensates of sulfonized polycyclic aromatic compounds which may have a three or more polymerized styrene sulfonic acid as an essential constituent or a hydrocarbon group as a substituent.

(B-7) benzalkonium salts represented by formula (VIII),

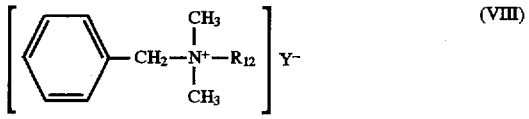
(VIII)

wherein $R_{12}$ represents a hydrocarbon group having 8–24 carbon atoms; and Y⁻ represents a halogen atom, amino acid, fatty acid, an anionic residue of phosphate, phosphonate, sulfonate, or sulfate having an alkyl or alkenyl group of branched or straight chain 1–30 carbon atoms, and an anionic oligomer or polymer selected from formalin condensates of sulfonized polycyclic aromatic compounds which may have a three or more polymerized styrene sulfonic acid as an essential constituent or a hydrocarbon group as a substituent.

Other than compounds (B-1)–(B-7), sulfur, selenium sulfide, cadmium sulfide, allantoin, menthols, salicylic acid, undecylenic acid, and the like may be used as the antibacterial agent.

The above-mentioned antibacterial agents can be used singly or as a mixture of one or more of them. The antibacterial agent is incorporated in the composition of the present invention in an amount of 0.01–5% by weight, and preferably 0.1–1.5% by weight.

The amount less than 0.01% by weight provides insufficient dandruff-preventive and deodorant effects. The amount greater than 5% by weight is undesirable because the effect will not increase while the irritation of the antibacterial agent causes a problem.

With the embodiment of the present invention, a desired antibacterial effect can be achieved using a small amount of antibacterial agent compared with conventional detergent compositions.

Any antibacterial agents can be used for the detergent compositions of the present invention insofar as they exhibit good antibacterial effect and are adaptable to the human body, however, those exemplified before are preferable. Especially for dandruff-preventive detergents, salts of mercaptopyridine oxide shown as compounds (B-1) and 1-hydroxy-2-pyridones shown as compounds (B-2); and for deodorant detergents, trichloro carbanide (TCC) shown as compounds (B-4) and trichlosan shown as compounds (B-5) are preferable as an antibacterial agent.

Besides the above essential components, the composition of the present invention may further comprise conventionally known components inasmuch as the effect of the present invention is not impaired. Such components may include various surfactants such as alkylsulfate, polyoxyethylenealkylsulfate, α-olefinalkylsulfate, half alkylsulfsuccinate, acylated glutamic acid, monoalkyl phosphate, soaps, and the like; water; humectants such as glycerol, propylene glycol, and the like; conditioning agents such as cationized cellulose and the like; viscosity-adjusting agents such as ethanol, hydroxyethyl cellulose, methyl cellulose, and the like; antiseptics such as methyl parabene, urea, and the like; antiphlogistics such as potassium glycyrrhizicate, and the like; UV-ray absorbers such as oxybenzone and the like; antioxidants such as dibutylhydroxytoluene, tocopherol acetate, and the like; pearlescent agents; perfumes; pigments; and the like.

The pH of the detergent compositions of the present invention may be adjusted to 2–10, preferably to 4–8 using an alkali or acid agent.

The detergent compositions of the present invention can be provided in any form used for conventional detergent compositions, e.g. solid, powder, cream, liquid.

Other features of the invention will become apparent in the course of the following description of the exemplary embodiments which are given for illustration of the invention and are not intended to be limiting thereof.

EXAMPLES

Example 1

Shampoo composition

A shampoo composition was prepared using 20% by weight of decylpolyglucoside [$R_1$: decyl group, G: glucose, m: 0, n: 1.3 in formula (I)] as a saccharide nonionic surfactant and 1% by weight of zincpyrithion (Zpt) as an antibacterial agent, and subjected to the test shown below to evaluate an anti-dandruff effect. A shampoo composition prepared using 20% by weight of laurylsulfate triethanolamine salt (anionic surfactant) and 1% by weight of zincpyrithion (Zpt) was used as a control. The results are shown in Table 1.

<Test method>

Four (4) men, age 20–32, who are annoyed by relatively large amount of dandruff and to whom ordinary dandruff shampoos give no anti-dandruff effect were selected as subjects.

For the control period, first, the hair and the scalp of the subject four men was washed with a shampoo prepared using laurylsulfate triethanolamine salt without Zpt over a period of two weeks and the state of dandruff was observed by the naked eye. Next, the above two shampoos were applied to the subject four men over a period of one month according to the half-head method. The state of dandruff after the one month period was observed, at right and left positions of the head respectively, by the naked eye, and compared with those of the scalps immediately after the control perod, to evaluate an anti-dandruff effect according to the following evaluation standard:

<Evaluation standard>

AAA: anti-dandruff effect is excellent.
BBB: anti-dandruff effect is slightly observed.
CCC: no anti-dandruff effect is observed.

TABLE 1

| Subject | Laurylsulfate triethanolamine salt and Zpt | Decylpoly-glucoside (S = 1.3) and Zpt |
|---|---|---|
| 1 | CCC | BBB |
| 2 | CCC | BBB |
| 3 | BBB | AAA |
| 4 | BBB | AAA |

The shampoo composition of the present invention exhibited significantly excellent anti-dandruff effect compared with a conventional shampoo composition containing an antibacterial agent.

Example 2

Body shampoo

| | % by weight |
|---|---|
| Decylpolyglucoside [$R_1$: decyl group, G: glucose, m: 0, n: 1.4 in formula (I)] | 10 |
| Triethanolamine laurylphosphate | 10 |
| Laurylhydroxysulfobetaine | 3 |
| Potassium glycyrrhizicate | 0.3 |
| Oxybenzone | 0.2 |
| trichlosan | 0.5 |
| Perfume | small amount |
| Water | balance |
| Total | 100 |

This body shampoo exhibited extremely low irritation to the skin and gave an excellent deodorant effect.

Example 3

Shampoo:

| | % by weight |
|---|---|
| Decylfructoside [$R_1$: decyl group, G: fructose, m: 0, n: 1.3 in formula (I)] | 15 |
| Lauric acid diethanolamide | 2 |
| Cationic polymer (Polymer JR400 manufactured by Union Carbide Co.) | 0.1 |
| 2-dodecylhexadecyltrimethyl ammonium chloride | 0.2 |

-continued

Shampoo:

| | % by weight |
|---|---|
| Zincpyrithion | 0.1 |
| Polyvinyl alcohol | 0.5 |
| Antiseptic | 0.1 |
| Perfume, Pigment | q.s. |
| Water | balance |
| Total | 100 |

This shampoo exhibited extremely low irritation to the skin and gave an excellent anti-dandruff effect.

Example 4

| | % by weight |
|---|---|
| N-methyl lauric acid glucamide [$R_3$: decyl group, $R_4$: methyl group, X: glucose in formula (II)] | 15 |
| Lauric acid diethanolamide | 2 |
| Cationic polymer (Merquat 550, manufactured by Merck Co.) | 0.1 |
| 2-dodecylhexadecyltrimethyl ammonium chloride | 0.2 |
| Octopirox, manufactured by Hoechst AG | 1.0 |
| Antiseptic | 0.1 |
| Perfume, Pigment | q.s. |
| Water | balance |
| Total | 100 |

This shampoo exhibited extremely low irritation to the skin and gave an excellent anti-dandruff effect.

The detergent compositions of the present invention are excellently mild to the skin, exhibiting a high antibacterial effect, without influencing or weakening the cutaneous metabolic and barrier functions of the skin.

Accordingly, when used as detergents for the scalp and the hair, the detergent compositions of the present invention can effectively restrain the early occurrence of dandruff after shampooing. They also exhibit high antibacterial effect when used as body detergents.

Obviously, numerous modifications and variations of the present invention are possible in light of the above teachings. It is therefore to be understood that within the scope of the appended claims, the invention may be practiced otherwise than as specifically described herein.

What is claimed is:

1. A detergent composition comprising:
   (a) 0.1 to 95% by weight of one or more saccharide nonionic surfactants selected from alkyl saccharide surfactants represented by:

$$R_1-O-(R_2O)_m-G_n \qquad (I)$$

wherein R1 represents a linear or branched alkyl, an alkenyl, or an alkylphenyl group having 6–18 carbon atoms, $R_2$ represents an alkylene group having 2–4 carbon atoms, G is a reducing sugar having 5–6 carbon atoms, m denotes a value of 0–10, and n denotes a value of 1–10, (b) 0.01 to 5% by weight of one or more antibacterial agents selected from the group consisting of:
      (i) calcium-, magnesium-, barium-, strontium-, zinc-, cadmium-, tin-, or zirconium salts of 2-mercapto-pyridine-N-oxide;

(c) a detergent effective amount of one or more surfactants selected from the group consisting of alkylsulfate, polyoxyethylenealkylsulfate, α-olefinalkylsulfate, alkylsulfosuccinate, acylated glutamic acid, monoalkyl phosphate and soaps.

2. A detergent composition consisting essentially of:

(a) 0.1 to 95% by weight of one or more saccharide nonionic surfactants selected from alkyl saccharide surfactants represented by:

wherein R1 represents a linear or branched alkyl, an alkenyl, or an alkylphenyl group having 6–18 carbon atoms, $R_2$ represents an alkylene group having 2–4 carbon atoms, G is a reducing sugar having 5–6 carbon atoms, m denotes a value of 0–10, and n denotes a value of 1–10, (b) 0.01 to 5% by weight of one or more antibacterial agents selected from the group consisting of:

(i) calcium-, magnesium-, barium-, strontium-, zinc-, cadmium-, tin-, or zirconium salts of 2-mercaptopyridine-N-oxide; and (ii) 1-hydroxy-2-pyrrolidone derivatives represented by formula (III),

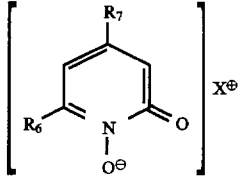

wherein $R_6$ represents an alkyl group having 1–17 carbon atoms, an alkenyl group having 2–17 carbon atoms, a cycloalkyl group having 5–8 carbon atoms, a bicycloalkyl group having 7–9 carbon atoms, a cycloalkyl-alkyl group wherein the alkyl group has 1–4 carbon atoms and the cycloalkyl group may be substituted with an alkyl group having 1–4 carbon atoms, an aryl group, an aralkyl group with an alkyl group having 1–4 carbon atoms, an arylalkenyl group with the alkenyl group having 2–4 carbon atoms, an aryloxyalkyl or an arylmercaptoalkyl group with the alkyl group having 1–4 carbon atoms, a benzhydryl group, a phenylsulfonylalkyl group with the alkyl group having 1–4 carbon atoms, a furylalkenyl group with the furyl or alkenyl group having 2–4 carbon atoms, wherein the above-mentioned aryl residual group may be substituted with an alkyl group having 1–4 carbon atoms, an alkoxy group having 1–4 carbon atoms, a nitro group, a cyano group, or a halogen atom; $R_7$ represents a hydrogen atom, an alkyl group having 1–4 carbon atoms, an alkenyl group having 2–4 carbon atoms, a halogen atom, a phenyl group, or a benzyl group; and $X^+$ represents an organic base, an alkali metal ion, an ammonium ion, an alkaline earth metal ion, or a divalent to tetravalent cationic ion;

(c) a detergent effective amount of one or more surfactants selected from the group consisting of alkylsulfate, polyoxyethylenealkylsulfate, α-olefinalkylsulfate, alkylsulfosuccinate, acylated glutamic acid, monoalkyl phosphate and soaps.

3. A detergent composition as claimed in claim 2, wherein component (c) is a detergent effective amount of one or more surfactants selected from the group consisting of alkylsulfate, polyoxyethylenealkylsulfate, α-olefinalkylsulfate, acylated glutamic acid, monoalkyl phosphate and soaps.

4. A detergent composition comprising:

(a) 0.1 to 95% by weight of one or more saccharide nonionic surfactants selected from alkyl saccharide surfactants represented by:

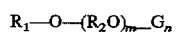

wherein R1 represents a linear or branched alkyl, an alkenyl, or an alkylphenyl group having 6–18 carbon atoms, $R_2$ represents an alkylene group having 2–4 carbon atoms, G is a reducing sugar having 5–6 carbon atoms, m denotes a value of 0–10, and n denotes a value of 1–10, (b) 0.01 to 5% by weight of one or more antibacterial agents selected from the group consisting of:

(i) calcium-, magnesium-, barium-, strontium-, zinc-, cadmium-, tin-, or zirconium salts of 2-mercaptopyridine-N-oxide; and (ii) 1-hydroxy-2-pyrrolidone derivatives represented by formula (III),

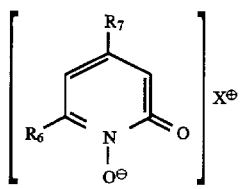

wherein $R_6$ represents an alkyl group having 1–17 carbon atoms, an alkenyl group having 2–17 carbon atoms, a cycloalkyl group having 5–8 carbon atoms, a bicycloalkyl group having 7–9 carbon atoms, a cycloalkyl-alkyl group wherein the alkyl group has 1–4 carbon atoms and the cycloalkyl group may be substituted with an alkyl group having 1–4 carbon atoms, an aryl group, an aralkyl group with an alkyl group having 1–4 carbon atoms, an arylalkenyl group with the alkenyl group having 2–4 carbon atoms, an aryloxyalkyl or an arylmercaptoalkyl group with the alkyl group having 1–4 carbon atoms, a benzhydryl group, a phenylsulfonylalkyl group with the alkyl group having 1–4 carbon atoms, a furylalkenyl group with the furyl or alkenyl group having 2–4 carbon atoms, wherein the above-mentioned aryl residual group may be substituted with an alkyl group having 1–4 carbon atoms, an alkoxy group having 1–4 carbon atoms, a nitro group, a cyano group, or a halogen atom; $R_7$ represents a hydrogen atom, an alkyl group having 1–4 carbon atoms, an alkenyl group having 2–4 carbon atoms, a halogen atom, a phenyl group, or a benzyl group; and $X^+$ represents an organic base, an alkali metal ion, an ammonium ion, an alkaline earth metal ion, or a divalent to tetravalent cationic ion;

(c) a detergent effective amount of one or more surfactants selected from the group consisting of acylated glutamic acid, monoalkyl phosphate and soaps.

5. The detergent composition as claimed in claim 4, wherein said component (c) is selected from the group consisting of acylated glutamic acid and monoalkyl phosphate.

6. The detergent composition as claimed in claim 4, consisting essentially of components (a), (b) and (c).

* * * * *

UNITED STATES PATENT AND TRADEMARK OFFICE
CERTIFICATE OF CORRECTION

PATENT NO. : 5,753,600
DATED : May 19, 1998
INVENTOR(S) : Jun KAMEGAI, et al.

It is certified that error appears in the above-identified patent and that said Letters Patent is hereby corrected as shown below:

On the title page, Item [30], the Foreign Application Priority Data has been omitted. It should read:

-- Oct. 9, 1989 [JP]     Japan........1-263680 --

Signed and Sealed this

Eighth Day of June, 1999

Attest:

Attesting Officer

Q. TODD DICKINSON

Acting Commissioner of Patents and Trademarks